United States Patent
Kitchen et al.

(12)

(10) Patent No.: US 6,350,901 B1
(45) Date of Patent: Feb. 26, 2002

(54) PROCESS FOR THE PRODUCTION OF VINYL ACETATE

(75) Inventors: Simon James Kitchen, Hillam (GB); George Frederick Salem, Shaker Heights, OH (US); Bruce Leo Williams, Elloughton Brough (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/363,011

(22) Filed: Jul. 29, 1999

(30) Foreign Application Priority Data

Aug. 11, 1998 (GB) ............................................. 9817365

(51) Int. Cl.⁷ ............................................ C07C 67/055
(52) U.S. Cl. ........................................ 560/245; 560/243
(58) Field of Search .................................. 560/243, 245

(56) References Cited

U.S. PATENT DOCUMENTS 3,380,834 A  *  4/1968  Kronig et al.
5,859,287 A  *  1/1999  Nicolau et al.

FOREIGN PATENT DOCUMENTS

| EP | A-0672453 | 9/1995 |
| EP | A-0685449 | 12/1995 |
| EP | 0 685 451 A1 * | 12/1995 |
| EP | A-0839793 | 5/1998 |
| EP | A-0847982 | 6/1998 |
| GB | 1266623 | 3/1972 |
| GB | 1266624 | 3/1972 |

* cited by examiner

*Primary Examiner*—Paul J. Killos
*Assistant Examiner*—Robert W. Deemie
(74) *Attorney, Agent, or Firm*—Nixon & Vanderhye

(57) ABSTRACT

In a process for production of vinyl acetate in which ethylene, liquid acetic acid and an oxygen-containing gas are fed to a fluid bed reactor containing a catalyst comprising a Group VIII metal, a promoter and a co-promoter, stickiness of the catalyst is reduced by limiting the amount of co-promoter to up to 6% by weight of the catalyst.

39 Claims, 1 Drawing Sheet

PROCESS FOR THE PRODUCTION OF VINYL ACETATE

The present invention relates to a process for the production of vinyl acetate.

BACKGROUND OF THE INVENTION

Vinyl acetate is generally prepared on a commercial basis by contacting acetic acid and ethylene with molecular oxygen in the presence of a catalyst active for the production of vinyl acetate.

A catalyst suitable for use in the production of vinyl acetate may comprise a Group VIII metal, a catalyst promoter and an optional co-promoter. For example EP A-0672453 discloses a process for the production of vinyl acetate by the catalytic oxidation of ethylene in the presence of acetic acid wherein the catalyst is a supported palladium catalyst comprising a promoter and a co-promoter.

It has been found that when the catalyst is used in a fluid bed reactor and the acetic acid is introduced into the reactor in the liquid form, the catalyst particles can become sticky and join together, thus forming lumps especially over extended periods of operation. In extreme cases, fluidisation can be lost which may cause the reactor to be shut down.

European patent publication EP-0847982-A relates to a fluid bed process for the production of vinyl acetate in which liquid is introduced into the fluidised bed reactor for the purpose of removing heat. The liquid introduced into the fluidised bed may be a reactant including the acetic acid reactant. Promoter such as potassium acetate may be dissolved in the liquid feed to the bed. In the example described therein the catalyst had a metal loading of 0.44 Pd, 0.36 Au and 2.5 K (weight %). This amount of potassium corresponds to 6.3 weight % potassium acetate. Although it is stated that the catalyst did not agglomerate and defluidise there is no indication of the scale of the experiment or how long the experiment was performed.

DESCRIPTION OF INVENTION

We have found that the problem of stickiness can be avoided by limiting the amount of co-promoter material in the catalyst composition.

Accordingly, the present invention provides a process for the production of vinyl acetate which comprises feeding ethylene, liquid acetic acid and an oxygen-containing gas into a fluid bed reactor and reacting at elevated temperature in the fluid bed reactor the ethylene, acetic acid and oxygen in the presence of a fluid bed catalyst material, said catalyst material comprising a Group VIII metal, a promoter and a co-promoter, said co-promoter being present in the reactor in an amount of up to 6% by weight of the catalyst.

The present invention provides a process for the production of vinyl acetate which avoids the problem of catalyst stickiness and ultimate lump formation, especially over extended periods of operation (for example greater than 7 days).

The catalyst of the present invention is a fluid bed catalyst material, comprising a Group VIII metal, a promoter and a co-promoter. These compounds are suitably accommodated on a support.

With regards to the Group VIII metal, the preferred metal is palladium. Suitable sources of palladium include palladium (II) chloride, sodium or potassium tetrachloropalladate, (II), ($Na_2PdCl_4$ or $K_2PdCl_4$), palladium acetate, $H_2PdCl4$, palladium (II) nitrate or palladium (II) sulphate. The metal may be present in a concentration of greater than 0.2% by weight, preferably greater than 0.5% by weight, especially about 1% by weight based upon total weight of catalyst. The metal concentration may be as high as 10% by weight.

In addition to the Group VIII metal, the catalyst comprises a promoter. Suitable promoters include gold, copper, cadmium and/or nickel compounds. A preferred promoter is gold. Suitable sources of gold include gold chloride, tetrachloroauric acid ($HAuCl_4$), $NaAuCl_4$, $KAuCl_4$, dimethyl gold acetate, barium acetoaurate or gold acetate. The preferred gold compound is $HAuCl_4$. The promoter metal may be present in an amount of from 0.1 to 10% by weight in the finished catalyst.

The catalyst composition comprises a co-promoter material present in a concentration of up to 6% by weight of the catalyst composition. Suitable co-promoters include Group I, Group II, lanthanide or transition metals, for example cadmium, barium, potassium, sodium, iron, manganese, nickel, antimony, and/or lanthanum, which are present in the finished catalyst as salts, e.g. an acetate salt. The preferred salts are potassium or sodium acetate. The co-promoter is present in the catalyst composition in a concentration of up to 6% by weight of catalyst. Preferably, the concentration is from 3.5 to 5.5% by weight of catalyst, especially about 5% by weight.

The catalyst material is a supported catalyst. Suitable catalyst supports include porous silica, alumina, silica/alumina, titania, silica/titania, zirconia or carbon. Preferably the support is silica. Suitably, the support may have a pore volume from 0.2 to 3.5 mL per gram of support, a surface area of 5 to 800 $m^2$ per gram of support and an apparent bulk density of 0.3 to 1.5 g/mL. The support may typically have a particle size distribution such that at least 60% of the catalyst particles have a particle diameter of below $2\times10^{-4}$m (200 microns). Preferably at least 50%, more preferably, at least 80%, most preferably, at least 90% of the catalyst particles have a particle diameter less than $1.05\times10^{-4}$m (105 microns). Preferably no more than 40% of the catalyst particles have a diameter of less than $4\times10^{-5}$m (40 microns).

The catalyst may be prepared by any suitable method, such as that detailed in EP-A-0672453. Suitably, the first stage of the catalyst preparation process involves impregnation of the support material with a solution containing the required Group VIII metal and the promoter metal in the form of soluble salts. Examples of such salts are soluble halide derivatives. The impregnating solution is preferably an aqueous solution and the volume of solution used is such that it corresponds to between 50 and 100% of the pore volume of the support, preferably 50 to 99% of the pore volume.

The impregnated support is dried at ambient or reduced pressure and from ambient temperature to 150° C., preferably 60 to 130° C. prior to metals reduction. To convert such materials into the metallic state, the impregnated support is treated with a reducing agent such as ethylene, hydrazine, formaldehyde or hydrogen. If hydrogen is used, it will usually be necessary to heat the catalyst to 100 to 850° C. in order to effect complete reduction.

After the steps described above have been carried out, the reduced catalyst is washed with water and then dried. The dried carrier is then impregnated with the required amount of co-promoter and thereafter dried. Alternatively, the wet, reduced, washed material is impregnated with co-promoter then dried.

The method of catalyst preparation may be varied to optimise catalyst performance based on maximising vinyl acetate yield and selectivity.

The process of the present invention comprises reacting ethylene, acetic acid and an oxygen-containing gas in the presence of the catalyst material. Ethylene may be used in substantially pure form or admixed with one or more of nitrogen, methane, ethane, carbon dioxide and water in the form of steam or one or more of hydrogen, $C_3/C_4$ alkenes or alkanes. The ethylene in the combined feed to the reactor may be at least 60 mole %.

The oxygen-containing gas may suitably be air or a gas richer or poorer in molecular oxygen than air. Suitably, the gas may be oxygen diluted with a suitable diluent, for example, nitrogen, argon or carbon dioxide. Preferably the gas is oxygen.

The acetic acid is introduced into the reactor in liquid form. Optionally, a portion of the acid may be introduced in the vapour form. The acetic acid is preferably crude acetic acid. Suitably, the liquid acetic acid may be introduced into the fluid bed reactor by any suitable injection means, for example a nozzle which may be a gas-induced atomising nozzle or liquid-only spray-type nozzles. One or more nozzles may be used for this purpose. Additionally, recycled acetic acid may be introduced into the reactor. The recycled acetic acid may be pre-mixed with the crude acetic acid or may be introduced into the reactor using a separate injection means. The recycled acetic acid may suitably comprise water. Suitably, the water concentration in the recycle stream is such that the water concentration being fed into the reactor is less than 6% by weight, preferably less than 4% more preferably, less than 3% of the total acid and water stream fed into the reactor. The usual precautions for introducing a liquid into a fluid bed should be taken, such as avoiding cold surfaces.

It is generally known in such catalytic processes that catalyst activity will decrease with time for various reasons. In particular, due to the volatile nature of the co-promoter, the level of co-promoter in the catalyst material decreases with time. This results in loss of catalyst activity and a loss in selectivity. In order to maintain a constant concentration of co-promoter on the catalyst, the concentration being less than 6 wt %, fresh co-promoter may be added to the catalyst during the reaction. This may suitably be carried out by adding the co-promoter material to the liquid acetic acid feed or to the liquid recycle acetic acid. Alternatively, the additional co-promoter may be introduced as a solution e.g. in water or in acid directly by spraying into the reactor through a suitable injection means such as a nozzle. In each case, the co-promoter contacts the catalyst material.

The process is carried out in a fluid bed reactor and may suitably be operated at a temperature from 100 to 400° C., preferably 140 to 210° C. and a pressure of $10^5$ to $2 \times 10^6$ Pa gauge (1 to 20 barg), preferably $6 \times 10^5$ to $1.5 \times 10^6$ Pa gauge (6 to 15 barg), especially $7 \times 10^5$ to $1.2 \times 10^6$ Pa gauge (7 to 12 barg).

BRIEF DESCRIPTION OF THE DRAWING

The present invention will now be illustrated with reference to FIG. 1 and the following Examples in which

The examples were carried out on a full recycle pilot plant which was operated at steady state. The apparatus is as shown in FIG. 1 and includes a feed system, reactor gas/liquid separation, gas recycle, product recovery and liquid recycle. With reference to FIG. 1, fresh acetic acid from storage (1) and recycle acetic acid are pumped together with some recycle gas (3) to twin fluid nozzle within the fluid bed (2). The remainder of the recycle gas feed (3), fresh ethylene (4) and oxygen (5) enter the plenum and through a sintered plate into the reactor. Fresh oxygen (6) may be fed directly into the fluid bed. A freeboard section is provided for disengaging the catalyst (7). The gaseous products exit the reactor through exit (8) through sintered filter elements (not shown). The reactor temperature is controlled using a pumped system where hot heat transfer fluid is passed through three jackets (not shown) attached to the reactor wall. All equipment is constructed out of 316L stainless steel.

Figure 1:
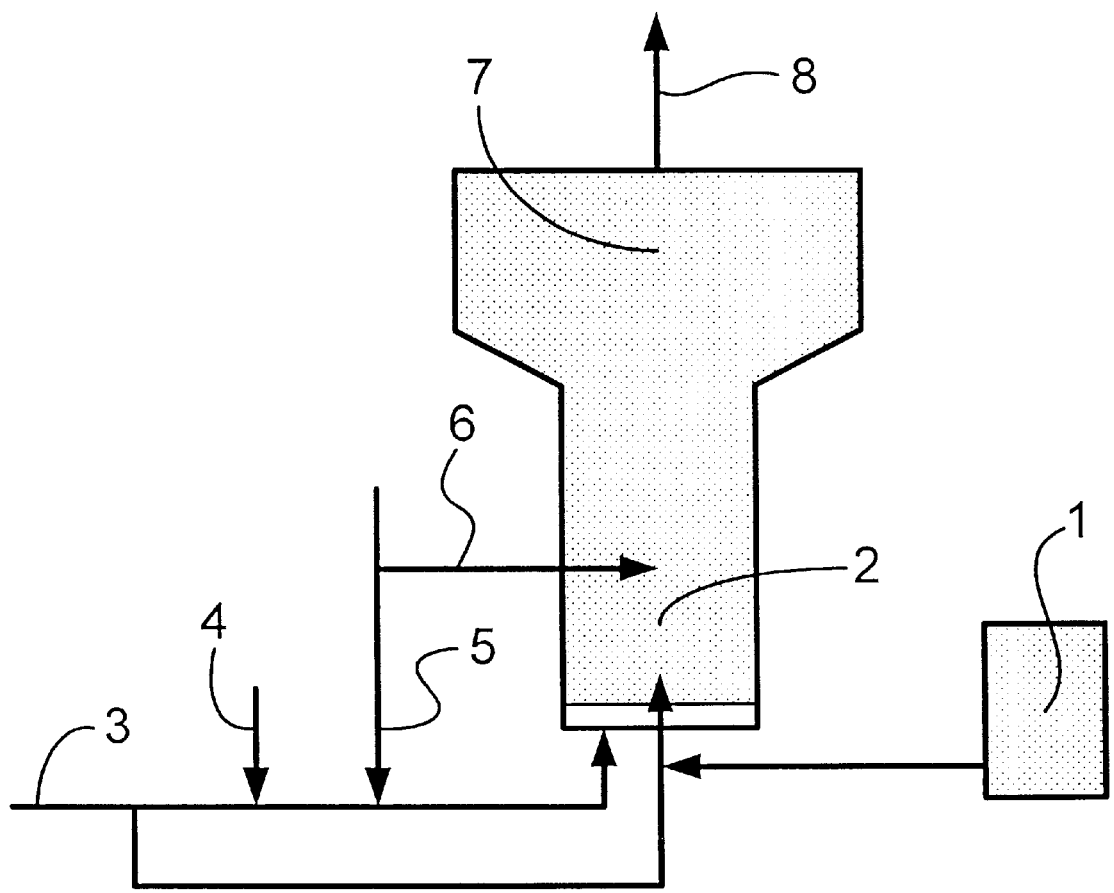
FIG. 1 is a schematic representation of a reactor system for use in the present invention.

Example 1 is an example according to the present invention. Comparative Example A is not according to the invention wherein the process uses a catalyst not according to the present invention in that it contains more than 6% by weight co-promoter.

EXAMPLES

Example 1
(a) Preparation of Catalyst Support

The support was prepared by spray drying a mixture of silica sol 1060 (obtained from Nalco Chemical Company) and Aerosil® silica (obtained from Degussa Chemical Company). In the dried support 80% of the silica sol came from the sol and 20% of the silica came from the Aerosil. The spray dried microspheres were calcined in air at 640° C. for 4 hours. The particle size distribution of the support which was used for the catalyst preparation is as follows:

| Particle size (microns) | % |
| --- | --- |
| $>3 \times 10^{-4}$ m (>300) | 2 |
| $4.4 \times 10^{-5}$ m–$3 \times 10^{-4}$ m (44–300) | 68 |
| $<4.4 \times 10^{-5}$ (<44) | 30 |

It should be understood that the particle size distribution given above is not intended to be limiting and that variations in this distribution are contemplated depending upon reactor size and operating conditions.

(b) Preparation of Catalyst

The silica support (54.4 kg) obtained from step (a) above was impregnated with a solution of $Na_2PdCl_4.xH_2O$ (containing 1000 g Pd) and $AuCl_4.xH_2O$ (containing 400 g Au) in distilled water by incipient wetness. The resulting mixture was mixed thoroughly, left to stand for 1 hour and dried overnight.

The impregnated material was then added slowly to a 5% solution of $N_2H_4$ in distilled water and the mixture allowed to stand with occasional stirring. Thereafter, the mixture was filtered and washed with 4×400 litres of distilled water. The resulting solid was dried overnight.

The material was impregnated with a solution of potassium acetate (2.8 kg) by incipient wetness. The resulting mixture was mixed thoroughly, left to stand for 1 hour and dried overnight. The catalyst was then screened to remove particles having a particle size greater than 106 microns.

The resulting catalyst comprised 1.45 wt % palladium, 0.65 wt % gold and 4.3 wt % potassium acetate.

(c) Production of Vinyl Acetate 4.5 kg of catalyst prepared according to step (b) above was loaded into the reactor. The reactor was operated at $8 \times 10^5$ Pa gauge (8 barg) with a bed temperature profile of: bottom 145° C., middle 152.5° C., top 155° C. The total feed composition in mole percent entering the catalyst bed was ethylene:oxygen:acetic acid:inerts 58.9:4.9:11:25.2 respectively at a total reactor inlet velocity of 13.2 cm/sec at process conditions with a twin fluid nozzle liquid to gas weight ratio of 2.05:1. The process was operated under these conditions in excess of 28 days with no operational upset.

Example A (Comparative Example)
a) Preparation of Catalyst Support.

The support was prepared as detailed in Example 1, above.

(b) Preparation of Catalyst

The silica support (54.4 kg) obtained from (a) above was impregnated with a solution of $Na_2PdCl_4.xH_2O$ (containing 1850 g Palladium) and $AuCl_4.xH_2O$ (containing 740 g Au) in distilled water by incipient wetness. The resulting mixture was mixed thoroughly, left to stand for 1 hour and dried overnight.

A portion of the impregnated material (18 kg) was added slowly to a 10% solution of $N_2H_4$ in distilled water and the mixture allowed to stand overnight with occasional stirring. Thereafter, the mixture was filtered and washed with 4×200 litres of distilled water. The solid was then dried overnight.

The material was impregnated with an aqueous solution of potassium acetate (1.4 kg) by incipient wetness. The resulting mixture was mixed thoroughly, left to stand 1 hour and dried overnight.

The resulting catalyst comprised 3.1 wt % palladium, 1.26 wt % gold and 6.3 wt % potassium acetate.

(c) Production of Vinyl Acetate 3.45 kg of catalyst prepared according to step (b) above containing 6.3 wt % potassium acetate was loaded to the reactor. The reactor was operated at $8\times10^5$ Pa gauge (8 barg) with a bed temperature profile of: bottom 150° C., middle 155° C., top 155° C. The total feed composition in mole percent entering the catalyst bed was ethylene:oxygen:acetic acid:inerts 47:3:22:28 respectively at a total reactor inlet velocity of 6.7 cm/sec at process conditions with a twin fluid nozzle liquid to gas weight ratio of 2.14:1. After 7 days of operation, the oxygen detected at the reactor exit suddenly increased with a fall in production rate to near zero. This suggested that the catalyst bed was not fluidising adequately and had probably become "sticky" so not mixing adequately with the gas feed. The process was shut down and the catalyst dried at 150° C. for 12 hours. Upon discharging the catalyst from the reactor both free flowing catalyst and lumps were recovered. The free flowing catalyst analysed for 2.1 wt % potassium, the lumps analysed for 4.8 wt % potassium. These results suggest migration had occurred when the bed became "sticky" and poorly fluidised.

We claim:

1. A process for the production of vinyl acetate which comprises feeding ethylene, liquid acetic acid and an oxygen-containing gas into a fluid bed reactor and reacting at elevated temperature in the fluid bed reactor the ethylene, acetic acid and oxygen in the presence of a fluid bed catalyst material, said catalyst material comprising a Group VIII metal, a promoter and a co-promoter, said co-promoter being present in the reactor in an amount of up to 6% by weight of the catalyst.

2. A process as claimed in claim 1 in which said Group VIII metal is present in a concentration of greater than 0.2% by weight of the weight of said catalyst and up to 10% by weight of the weight of said catalyst.

3. A process as claimed in claim 2 in which said Group VIII metal is palladium.

4. A process as claimed in claim 3 in which said promoter is present in an amount of from 0.1 to 10% by weight as metal in said catalyst material.

5. A process as claimed in claim 4 in which said promoter is selected from the group consisting of gold, copper, cadmium, nickel and mixtures thereof.

6. A process as claimed in claim 1 in which said co-promoter is selected from the group consisting of salts of Group I, Group II, lanthanides and transition metals.

7. A process as claimed in claim 6 in which said co-promoter is selected from the group consisting of salts of cadmium, barium, potassium, sodium, iron, manganese, nickel, antimony, lanthanum and mixtures thereof.

8. A process as claimed in claim 5 in which said co-promoter is selected from the group consisting of salts of Group I, Group II, lanthanides and transition metals.

9. A process as claimed in claim 8 in which said co-promoter is selected from the group consisting of salts of cadmium, barium, potassium, sodium, iron, manganese, nickel, antimony, lanthanum and mixtures thereof.

10. A process as claimed in claim 1 in which said co-promoter is present in a concentration from 3.5 to 5.5% by weight of said catalyst.

11. A process as claimed in claim 2 in which said co-promoter is present in a concentration from 3.5 to 5.5% by weight of said catalyst.

12. A process as claimed in claim 5 in which said co-promoter is present in a concentration from 3.5 to 5.5% by weight of said catalyst.

13. A process as claimed in claim 6 in which said co-promoter is present in a concentration from 3.5 to 5.5% by weight of said catalyst.

14. A process as claimed in claim 7 in which said co-promoter is present in a concentration from 3.5 to 5.5% by weight of said catalyst.

15. A process as claimed in claim 8 in which said co-promoter is present in a concentration from 3.5 to 5.5% by weight of said catalyst.

16. A process as claimed in claim 9 in which said co-promoter is present in a concentration from 3.5 to 5.5% by weight of said catalyst.

17. A process as claimed in claim 1 in which co-promoter is added to said catalyst during the reaction.

18. A process as claimed in claim 17 in which said added co-promoter is added to said liquid acetic acid feed or to a liquid recycle acetic acid.

19. A process as claimed in claim 17 in which said added co-promoter is added as a solution sprayed into said reactor through injection means.

20. A process as claimed in claim 19 in which said added co-promoter is added as a solution in water or in acid.

21. A process as claimed in claim 7 in which co-promoter is added to said catalyst during the reaction.

22. A process as claimed in claim 21 in which said added co-promoter is added to said liquid acetic acid feed or to a liquid recycle acetic acid.

23. A process as claimed in claim 21 in which said added co-promoter is added as a solution sprayed into said reactor through injection means.

24. A process as claimed in claim 23 in which said added co-promoter is added as a solution in water or in acid.

25. A process as claimed in claim 9 in which co-promoter is added to said catalyst during the reaction.

26. A process as claimed in claim 25 in which said added co-promoter is added to said liquid acetic acid feed or to a liquid recycle acetic acid.

27. A process as claimed in claim 25 in which said added co-promoter is added as a solution sprayed into said reactor through injection means.

28. A process as claimed in claim 27 in which said added co-promoter is added as a solution in water or in acid.

29. A process as claimed in claim 16 in which co-promoter is added to said catalyst during the reaction.

30. A process as claimed in claim 29 in which said added co-promoter is added to said liquid acetic acid feed or to a liquid recycle acetic acid.

31. A process as claimed in claim 29 in which said added co-promoter is added as a solution sprayed into said reactor through injection means.

32. A process as claimed in claim 31 in which said added co-promoter is added as a solution in water or in acid.

33. A process as claimed in claim 1 in which said co-promoter is present in a concentration of about 5% by weight of said catalyst.

34. A process as claimed in claim 2 in which said co-promoter is present in a concentration of about 5% by weight of said catalyst.

35. A process as claimed in claim 5 in which said co-promoter is present in a concentration of about 5% by weight of said catalyst.

36. A process as claimed in claim 6 in which said co-promoter is present in a concentration of about 5% by weight of said catalyst.

37. A process as claimed in claim 7 in which said co-promoter is present in a concentration of about 5% by weight of said catalyst.

38. A process as claimed in claim 8 in which said co-promoter is present in a concentration of about 5% by weight of said catalyst.

39. A process as claimed in claim 9 in which said co-promoter is present in a concentration of about 5% by weight of said catalyst.

* * * * *

UNITED STATES PATENT AND TRADEMARK OFFICE
CERTIFICATE OF CORRECTION

PATENT NO.    : 6,350,901 B1
DATED         : February 26, 2002
INVENTOR(S)   : Kitchen et al.

It is certified that error appears in the above-identified patent and that said Letters Patent is hereby corrected as shown below:

<u>Column 5, line 47 to Column 8, line 13,</u>
Please substitute claims 1-39 with the present claims. Accordingly, claims 1-39 are renumbered as claims 1-78 as follows:

1. A process for the production of vinyl acetate which comprises feeding ethylene, liquid acetic acid and an oxygen-containing gas into a fluid bed reactor and reacting at elevated temperature of from 100 to 400°C in the fluid bed reactor the ethylene, acetic acid and oxygen in the presence of a fluid bed catalyst material, said catalyst material comprising a Group VIII metal, a promoter metal selected from the group consisting of gold, copper and cadmium and a co-promoter salt, said co-promoter salt being maintained in the reactor for a period of greater than 7 days in an amount of up to 6% by weight of the catalyst, whereby catalyst stickiness is avoided.

2. A process as claimed in claim 1 in which said Group VIII metal is present in a concentration of greater than 0.2 % by weight of the weight of said catalyst and up to 10 % by weight of the weight of said catalyst.

3. A process as claimed in claim 2 in which said Group VIII metal is palladium.

4. A process as claimed in claim 3 in which said promoter is present in an amount of from 0.1 to 10 % by weight as metal in said catalyst material.

5. A process as claimed in claim 4 in which said promoter is gold.

6. A process as claimed in claim 1 in which said co-promoter is selected from the group consisting of salts of Group I, Group II, lanthanides and transition metals.

UNITED STATES PATENT AND TRADEMARK OFFICE
CERTIFICATE OF CORRECTION

PATENT NO.     : 6,350,901 B1
DATED          : February 26, 2002
INVENTOR(S)    : Kitchen et al.

It is certified that error appears in the above-identified patent and that said Letters Patent is hereby corrected as shown below:

7. A process as claimed in claim 6 in which said co-promoter is selected from the group consisting of salts of cadmium, barium, potassium, sodium, iron, manganese, nickel, antimony, lanthanum and mixtures thereof.

8. A process as claimed in claim 5 in which said co-promoter is selected from the group consisting of salts of Group I, Group II, lanthanides and transition metals.

9. A process as claimed in claim 8 in which said co-promoter is selected from the group consisting of salts of cadmium, barium, potassium, sodium, iron, manganese, nickel, antimony, lanthanum and mixtures thereof.

10. A process as claimed in claim 1 in which said co-promoter is maintained at a concentration from 3.5 to 5.5 % by weight of said catalyst.

11. A process as claimed in claim 2 in which said co-promoter is maintained at a concentration from 3.5 to 5.5 % by weight of said catalyst.

12. A process as claimed in claim 5 in which said co-promoter is maintained at a concentration from 3.5 to 5.5 % by weight of said catalyst.

13. A process as claimed in claim 6 in which said co-promoter is maintained at a concentration from 3.5 to 5.5 % by weight of said catalyst.

14. A process as claimed in claim 7 in which said co-promoter is maintained at a concentration from 3.5 to 5.5 % by weight of said catalyst.

15. A process as claimed in claim 8 in which said co-promoter is maintained at a concentration from 3.5 to 5.5 % by weight of said catalyst.

16. A process as claimed in claim 9 in which said co-promoter is maintained at a concentration from 3.5 to 5.5 % by weight of said catalyst.

17. A process as claimed in claim 1 in which co-promoter is added to said catalyst during the reaction.

18. A process as claimed in claim 17 in which said added co-promoter is added to said liquid acetic acid feed or to a liquid recycle acetic acid.

19. A process as claimed in claim 17 in which said added co-promoter is added as a solution sprayed into said reactor through injection means.

20. A process as claimed in claim 19 in which said added co-promoter is added as a solution in water or in acid.

21. A process as claimed in claim 7 in which co-promoter is added to said catalyst during the reaction.

UNITED STATES PATENT AND TRADEMARK OFFICE
CERTIFICATE OF CORRECTION

PATENT NO. : 6,350,901 B1
DATED : February 26, 2002
INVENTOR(S) : Kitchen et al.

It is certified that error appears in the above-identified patent and that said Letters Patent is hereby corrected as shown below:

22. A process as claimed in claim 21 in which said added co-promoter is added to said liquid acetic acid feed or to a liquid recycle acetic acid.

23. A process as claimed in claim 21 in which said added co-promoter is added as a solution sprayed into said reactor through injection means.

24. A process as claimed in claim 23 in which said added co-promoter is added as a solution in water or in acid.

25. A process as claimed in claim 9 in which co-promoter is added to said catalyst during the reaction.

26. A process as claimed in claim 25 in which said added co-promoter is added to said liquid acetic acid feed or to a liquid recycle acetic acid.

27. A process as claimed in claim 25 in which said added co-promoter is added as a solution sprayed into said reactor through injection means.

28. A process as claimed in claim 27 in which said added co-promoter is added as a solution in water or in acid.

29. A process as claimed in claim 16 in which co-promoter is added to said catalyst during the reaction.

30. A process as claimed in claim 29 in which said added co-promoter is added to said liquid acetic acid feed or to a liquid recycle acetic acid.

31. A process as claimed in claim 29 in which said added co-promoter is added as a solution sprayed into said reactor through injection means.

32. A process as claimed in claim 31 in which said added co-promoter is added as a solution in water or in acid.

33. A process as claimed in claim 1 in which said co-promoter is maintained at a concentration of about 5% by weight of said catalyst.

34. A process as claimed in claim 2 in which said co-promoter is maintained at a concentration of about 5% by weight of said catalyst.

35. A process as claimed in claim 5 in which said co-promoter is maintained at a concentration of about 5% by weight of said catalyst.

36. A process as claimed in claim 6 in which said co-promoter is maintained at a concentration of about 5% by weight of said catalyst.

37. A process as claimed in claim 7 in which said co-promoter is maintained at a concentration of about 5% by weight of said catalyst.

UNITED STATES PATENT AND TRADEMARK OFFICE
CERTIFICATE OF CORRECTION

PATENT NO. : 6,350,901 B1
DATED : February 26, 2002
INVENTOR(S) : Kitchen et al.

It is certified that error appears in the above-identified patent and that said Letters Patent is hereby corrected as shown below:

38. A process as claimed in claim 8 in which said co-promoter is maintained at a concentration of about 5% by weight of said catalyst.

39. A process as claimed in claim 9 in which said co-promoter is maintained at a concentration of about 5% by weight of said catalyst.

40. A process for the production of vinyl acetate which comprises feeding ethylene, liquid acetic acid and an oxygen-containing gas into a fluid bed reactor and reacting at elevated temperature of from 100 to 400°C in the fluid bed reactor the ethylene, acetic acid and oxygen in the presence of a fluid bed catalyst material, said catalyst material comprising a Group VIII metal, a promoter and a co-promoter selected from the group consisting of salts of Group I, Group II and lanthanides, said co-promoter being maintained in the reactor for a period of greater than 7 days in an amount of up to 6% by weight of the catalyst, whereby catalyst stickiness is avoided.

41. A process as claimed in claim 40 in which said Group VIII metal is present in a concentration of greater than 0.2 % by weight of the weight of said catalyst and up to 10 % by weight of the weight of said catalyst.

42. A process as claimed in claim 41 in which said Group VIII metal is palladium.

43. A process as claimed in claim 42 in which said promoter is present in an amount of from 0.1 to 10 % by weight as metal in said catalyst material.

44. A process as claimed in claim 43 in which said promoter is selected from the group consisting of gold, copper, cadmium, nickel and mixtures thereof.

45. A process as claimed in claim 40 in which said co-promoter is selected from the group consisting of salts of Group I and Group II.

46. A process as claimed in claim 45 in which said co-promoter is selected from the group consisting of salts of barium, potassium, sodium and mixtures thereof.

47. A process as claimed in claim 44 in which said co-promoter is selected from the group consisting of salts of Group I and Group II.

48. A process as claimed in claim 47 in which said co-promoter is selected from the group consisting of salts of barium, potassium, sodium and mixtures thereof.

49. A process as claimed in claim 40 in which said co-promoter is maintained at a concentration from 3.5 to 5.5 % by weight of said catalyst.

50. A process as claimed in claim 41 in which said co-promoter is maintained at a concentration from 3.5 to 5.5 % by weight of said catalyst.

UNITED STATES PATENT AND TRADEMARK OFFICE
CERTIFICATE OF CORRECTION

PATENT NO. : 6,350,901 B1
DATED : February 26, 2002
INVENTOR(S) : Kitchen et al.

It is certified that error appears in the above-identified patent and that said Letters Patent is hereby corrected as shown below:

51. A process as claimed in claim 44 in which said co-promoter is maintained at a concentration from 3.5 to 5.5 % by weight of said catalyst.

52. A process as claimed in claim 45 in which said co-promoter is maintained at a concentration from 3.5 to 5.5 % by weight of said catalyst.

53. A process as claimed in claim 46 in which said co-promoter is maintained at a concentration from 3.5 to 5.5 % by weight of said catalyst.

54. A process as claimed in claim 47 in which said co-promoter is maintained at a concentration from 3.5 to 5.5 % by weight of said catalyst.

55. A process as claimed in claim 48 in which said co-promoter is maintained at a concentration from 3.5 to 5.5 % by weight of said catalyst.

56. A process as claimed in claim 40 in which co-promoter is added to said catalyst during the reaction.

57. A process as claimed in claim 56 in which said added co-promoter is added to said liquid acetic acid feed or to a liquid recycle acetic acid.

58. A process as claimed in claim 56 in which said added co-promoter is added as a solution sprayed into said reactor through injection means.

59. A process as claimed in claim 58 in which said added co-promoter is added as a solution in water or in acid.

60. A process as claimed in claim 46 in which co-promoter is added to said catalyst during the reaction.

61. A process as claimed in claim 60 in which said added co-promoter is added to said liquid acetic acid feed or to a liquid recycle acetic acid.

62. A process as claimed in claim 60 in which said added co-promoter is added as a solution sprayed into said reactor through injection means.

63. A process as claimed in claim 62 in which said added co-promoter is added as a solution in water or in acid.

64. A process as claimed in claim 48 in which co-promoter is added to said catalyst during the reaction.

65. A process as claimed in claim 64 in which said added co-promoter is added to said liquid acetic acid feed or to a liquid recycle acetic acid.

66. A process as claimed in claim 64 in which said added co-promoter is added as a solution sprayed into said reactor through injection means.

UNITED STATES PATENT AND TRADEMARK OFFICE
CERTIFICATE OF CORRECTION

PATENT NO.     : 6,350,901 B1
DATED          : February 26, 2002
INVENTOR(S)    : Kitchen et al.

It is certified that error appears in the above-identified patent and that said Letters Patent is hereby corrected as shown below:

67. A process as claimed in claim 66 in which said added co-promoter is added as a solution in water or in acid.

68. A process as claimed in claim 55 in which co-promoter is added to said catalyst during the reaction.

69. A process as claimed in claim 68 in which said added co-promoter is added to said liquid acetic acid feed or to a liquid recycle acetic acid.

70. A process as claimed in claim 68 in which said added co-promoter is added as a solution sprayed into said reactor through injection means.

71. A process as claimed in claim 70 in which said added co-promoter is added as a solution in water or in acid.

72. A process as claimed in claim 40 in which said co-promoter is maintained at a concentration of about 5% by weight of said catalyst.

73. A process as claimed in claim 41 in which said co-promoter is maintained at a concentration of about 5% by weight of said catalyst.

74. A process as claimed in claim 44 in which said co-promoter is maintained at a concentration of about 5% by weight of said catalyst.

75. A process as claimed in claim 45 in which said co-promoter is maintained at a concentration of about 5% by weight of said catalyst.

76. A process as claimed in claim 46 in which said co-promoter is maintained at a concentration of about 5% by weight of said catalyst.

77. A process as claimed in claim 47 in which said co-promoter is maintained at a concentration of about 5% by weight of said catalyst.

78. A process as claimed in claim 48 in which said co-promoter is maintained at a concentration of about 5% by weight of said catalyst.

Signed and Sealed this

Sixth Day of May, 2003

JAMES E. ROGAN
*Director of the United States Patent and Trademark Office*